United States Patent
Agnew et al.

(10) Patent No.: US 8,556,960 B2
(45) Date of Patent: Oct. 15, 2013

(54) FRAMELESS VASCULAR VALVE

(75) Inventors: Charles W. Agnew, West Lafayette, IN (US); Umesh H. Patel, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 215 days.

(21) Appl. No.: 12/613,326

(22) Filed: Nov. 5, 2009

(65) Prior Publication Data

US 2010/0114307 A1 May 6, 2010

Related U.S. Application Data

(60) Provisional application No. 61/111,904, filed on Nov. 6, 2008.

(51) Int. Cl.
*A61F 2/06* (2013.01)

(52) U.S. Cl.
USPC .......................................................... 623/1.24

(58) Field of Classification Search
USPC ...................... 623/1.24, 23.68, 2.12, 2.13, 2.1
See application file for complete search history.

(56) References Cited

U.S. PATENT DOCUMENTS

| | | |
|---|---|---|
| 4,218,782 A | 8/1980 | Rygg |
| 5,358,518 A | 10/1994 | Camilli |
| 5,855,601 A | 1/1999 | Bessler et al. |
| 6,092,529 A | 7/2000 | Cox |
| 6,126,686 A | 10/2000 | Badylak et al. |
| 2002/0177894 A1 | 11/2002 | Acosta et al. |
| 2003/0055492 A1* | 3/2003 | Shaolian et al. ............ 623/1.24 |
| 2005/0240262 A1* | 10/2005 | White ......................... 623/2.12 |

* cited by examiner

*Primary Examiner* — Wililam H. Matthews
(74) *Attorney, Agent, or Firm* — Woodard, Emhardt, Moriarty, McNett & Henry LLP

(57) ABSTRACT

Prosthetic valve devices, as well as systems and methods for the delivery thereof, are disclosed. A device includes one or more leaflets disposed within a frameless conduit, wherein the conduit is adapted for attachment to walls of a vascular vessel, and the leaflets are adapted for attachment to walls of the conduit. The leaflets are configured to selectively restrict blood flow through the conduit, and the conduit can include wall-engaging adaptations, for example, barbs or an adhesive. The conduit and the leaflets are formed with a flexible material, which may comprise a remodelable material and/or a synthetic polymer.

24 Claims, 11 Drawing Sheets

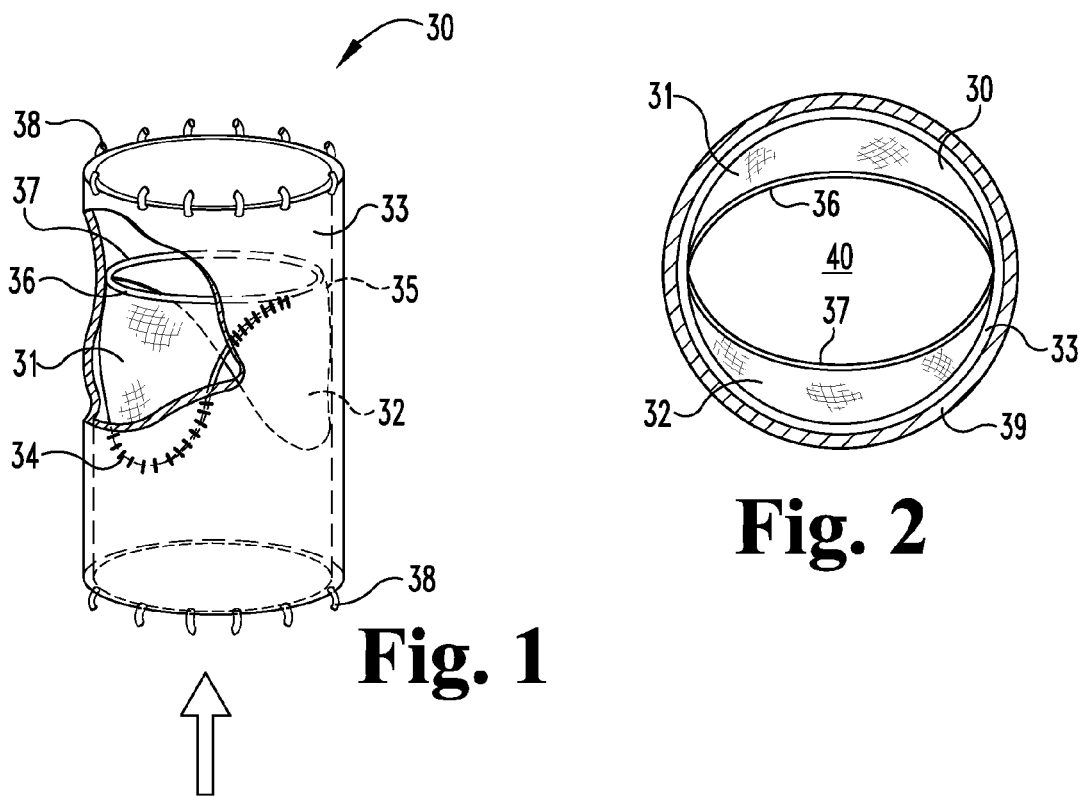
Fig. 1
Fig. 2
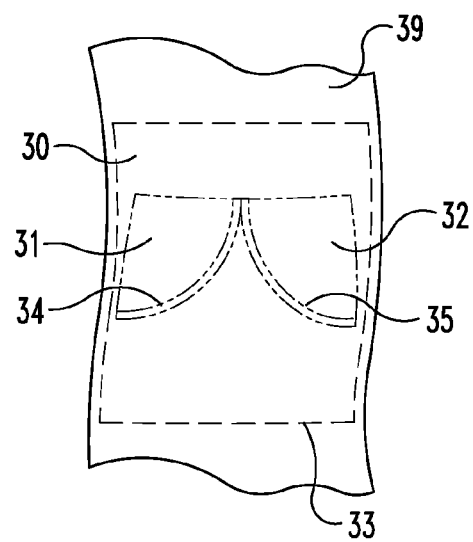
Fig. 3

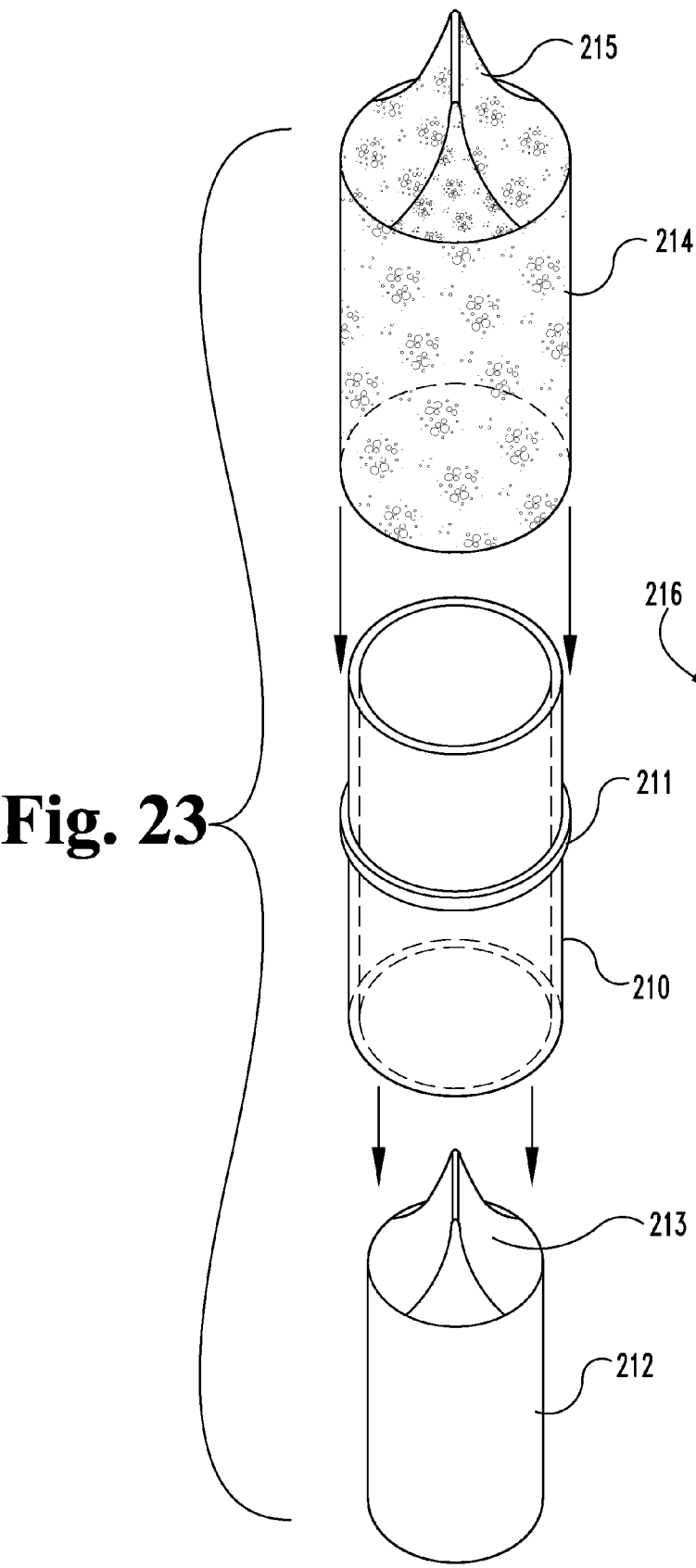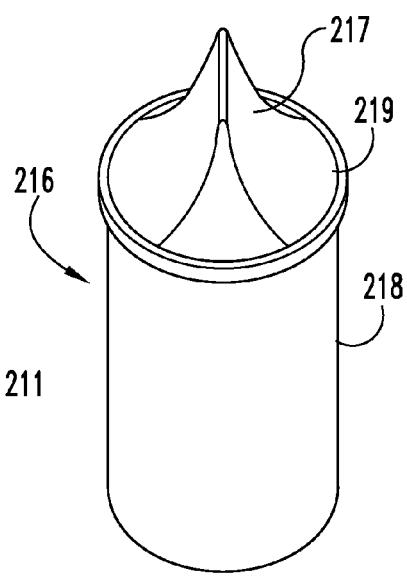
Fig. 23
Fig. 24

FRAMELESS VASCULAR VALVE

REFERENCE TO RELATED APPLICATIONS

The present application claims the benefit of U.S. Provisional Patent Application Ser. No. 61/111,904 filed Nov. 6, 2008, entitled "FRAMELESS VASCULAR VALVE," which is hereby incorporated by reference in its entirety.

BACKGROUND

The present invention relates generally to medical devices and in particular aspects to implantable prosthetic valves.

It is well understood in human pathology that the proper functioning of cardiac and venous valves is of the utmost importance. Numerous studies have shown that diseased cardiac valves cause significant morbidity and mortality and that incompetent or damaged venous valves often result in adverse medical conditions, especially in the lower extremities.

By preventing retrograde blood flow, the valves found throughout the venous system assist the flow of blood through the veins and returning to the heart. Venous valves are usually of the bicuspid type, with each cusp or leaflet forming a reservoir for blood, which, under pressure, forces the free edges of the cusps together to permit mostly antegrade blood flow to the heart. As a majority of venous blood flow is against gravity while a person is standing, incompetent or damaged venous valves can cause significant medical problems in the legs, ankles, and feet. There are at least two chronic venous diseases in which venous valve incompetence is thought to be an important factor: chronic venous insufficiency and varicose vein syndrome.

Chronic venous insufficiency involves venous hypertension and chronic venous stasis due to valvular incompetence. It has been estimated that in the United States chronic venous insufficiency associated with skin changes and ulcers affects six to seven million people. Varicose vein syndrome involves vein dilation or enlargement. According to another estimate, varicose veins affect about 4% of the adult western population, and approximately half of this population has significant varicose vein syndrome for which treatment will be sought.

Turning now to the cardiovascular system, incompetent or destroyed heart valves are a common form of heart disease, the leading cause of death in the United States. Although reconstructive surgery has been shown to be superior to valve replacement surgery in some respects, it is difficult to perform and not always possible in every patient. As a result, the vast majority of patients with diseased heart valves undergo valve replacement surgery, which involves removing a native valve and replacing it with a prosthetic one. Prosthetic heart valves come in various shapes and sizes and can be formed with a variety of materials. Often, the design of a prosthetic valve depends on the characteristics of the valve being replaced (e.g., mitral, aortic, tricuspid, or pulmonary) and/or the size of the patient's heart.

A variety of prosthetic valves have been developed in the art to treat conditions of the cardiovascular and venous systems. One such valve is defined by a tubular wall and one or more flexible leaflets. The leaflets are integrally connected to the tubular wall and converge axially along at least one commissure. The leaflets are designed to open and close the valve in response to pressure differentials across the valve. In an open, flow-conducting configuration, the free edges of adjacent leaflets are forced apart to form a conduit through which blood can flow. In a closed, flow-restricting configuration, the free edges of adjacent leaflets are forced together to form a closure, which eliminates or greatly reduces back flow through the valve.

There remain needs for improved and/or alternative prosthetic valve devices, as well as methods for preparing and utilizing the same. The present invention is addressed to those needs.

SUMMARY

In one embodiment, the present invention provides a valve device that comprises one or more leaflets disposed within a frameless conduit. The conduit may be formed with a tube of material or a sheet of material formed into a tube. The conduit is adapted for attachment to walls of a vascular vessel, whereas the leaflets are adapted for attachment to walls of the conduit. The leaflets are configured to selectively restrict blood flow through the conduit, with the leaflets and the conduit both being formed with a flexible material. In certain devices, the conduit and/or the leaflets can comprise a remodelable material and/or synthetic polymeric material. Desirably, the remodelable material comprises an extracellular matrix (ECM) material such as but not limited to small intestinal submucosa (SIS). In certain other devices, the conduit includes wall-engaging adaptations, such as barbs, adhesives, and the like, for attaching the conduit to the walls of the vessel. In still other devices, the leaflets have an edge that is attached to walls of the conduit. The leaflets may be attached to the conduit in any suitable manner, including but not limited to suturing, welding, gluing, and/or the like. In some forms, leaflets will be provided with reinforced edges. In preferred devices, the leaflets comprise a remodelable material, wherein portions of the leaflets can contact walls of the vessel through one or more apertures in the conduit, and thereby promote native tissue ingrowth into the leaflets from the walls of the vessel.

In another embodiment, the invention provides a frameless vascular valve comprising an inner conduit received concentrically within an outer conduit, wherein both conduits have a first end and a second end. The outer conduit first end provides material extending beyond the inner conduit first end to form a leaflet. The leaflet is configured to selectively restrict blood flow through the inner conduit, and can include a controlled reflux hole therein. In preferred devices, the inner conduit and the outer conduit are formed with a remodelable material and in particular SIS. In other preferred devices, the outer conduit is more flexible than the inner conduit to facilitate leaflet function. In these latter devices, the inner conduit can have a wall thickness greater than that of the outer conduit. Illustratively, the inner conduit might be formed with a multilaminate material, while the outer conduit is formed with a monolaminate material. In other devices, the inner conduit material is cross-linked to make it more rigid than the outer conduit material.

In a further embodiment, the invention provides a frameless valve prosthesis comprising a conduit element and a valve element, wherein both elements comprise a remodelable material. The valve element has a base that is integral with one end of the conduit element. In some devices, the base of the valve element is reinforced. In other devices, both elements further comprise a synthetic polymer.

In another embodiment, an inventive medical product includes any of the valve prostheses described herein in combination with a percutaneous deployment device. In some forms, the percutaneous deployment device will comprise at least one expandable element (e.g., a balloon) configured to selectively force portions of said valve prosthesis against inner walls of a vein.

In yet another embodiment, provided is a method for attaching any of the frameless valve prostheses of the present invention to a wall of a vein. In a preferred method, a valve is percutaneously attached to a wall of a vein. In another preferred method, a prosthesis is surgically attached to a wall of a vein, wherein the valve's conduit is sutured to the luminal surface of the vein.

In yet another embodiment, the invention provides a medical device that includes any of the frameless valves of the present invention and a percutaneous deployment device, wherein the deployment device has at least one expandable element adapted to selectively force portions of the valve against inner walls of a vein. Suitable frameless valves are as described above. Suitable percutaneous deployment devices may include a balloon catheter.

The invention also provides a method of modifying blood flow in a vascular vessel, wherein a prosthetic valve, such as one of the valves described above, is percutaneously delivered to a site within a vascular vessel. This method further includes percutaneously attaching at least a portion of the valve prosthesis to walls of the vascular vessel, whereby the prosthesis is able to selectively permit blood flow in a first direction and selectively restrict blood flow in a second direction.

In another aspect, the invention provides a method of manufacturing a valve prosthesis. This method comprises placing a conduit, at least a portion of which is formed with a remodelable material, between an inner mold and an outer mold. The inner mold and the outer mold both have a valve-shaping element at one end, wherein the two valve-shaping elements fit together when the inner mold is received within the outer mold. This method further comprises manipulating the conduit while the conduit is seated between the molds. Such manipulation at least partially forms the valve prosthesis, and may include but is not limited to vacuum pressing, freeze drying, cross linking, and the like. The prosthesis includes a conduit element and a valve element, wherein the valve element is located at one end of the conduit element, and is configured to selectively restrict blood flow through the conduit element. In certain devices, the valve element includes a reinforced base.

The invention further provides a method of manufacturing prosthetic valve that includes disposing at least one leaflet within a frameless conduit, wherein the leaflets are configured for attachment to the conduit to selectively restrict blood flow through the conduit. In some devices, the leaflets are configured to extend longitudinally along and at least partially circumferentially around the conduit. At least a portion of the conduit and at least a portion of the leaflet are formed with a remodelable material.

In another embodiment, the present invention includes a method of manufacturing a valve prosthesis that comprises providing a sheet of material having a leaflet-forming portion, wherein at least a portion of the sheet is formed with a remodelable material. This method further comprises connecting opposing sides of the sheet to form a conduit, whereupon the leaflet-forming portion provides a leaflet that is disposed within the conduit to selectively restrict blood flow through the conduit.

In yet another aspect, the invention provides a method of manufacturing a valve prosthesis, wherein a tube of material having walls is provided. At least a portion of the tube is formed with a remodelable material, and in preferred prostheses, the tube comprises submucosa. In certain devices, material contiguous with the walls of the tube is cut to form at least one leaflet. In other devices, portions of the walls are bent or forced inward to form one or more leaflets. In any of these devices, the leaflets are adapted to selectively restrict blood flow through the tube. In certain other devices, sutures are applied along a base and sides of the leaflet for reinforcement or support.

In another embodiment, the present invention provides a method of manufacturing a valve prosthesis, which comprises providing an inner conduit having at least one slit in a side wall thereof, and providing an outer conduit having at least one leaflet integrally formed therewith. At least a portion of the inner conduit and at least a portion of the outer conduit are formed with a remodelable material. The method further comprises receiving the outer conduit over the inner conduit, whereupon the leaflet is passed through the slit in the inner conduit to dispose the leaflet within the inner conduit. The leaflet is configured to selectively restrict blood flow through the inner conduit.

Other objects, embodiments, forms, features, advantages, aspects, and benefits of the present invention shall become apparent from the detailed description and drawings included herein.

BRIEF DESCRIPTION OF THE DRAWINGS

FIG. 1 provides a perspective view of one valve device of the invention.

FIG. 2 provides a top view of the valve device of FIG. 1 implanted within a vascular vessel.

FIG. 3 provides a side view of the valve device of FIG. 1 implanted within a vascular vessel.

FIG. 23 provides an exploded perspective view of one step in forming an illustrative valve device of the invention.

FIG. 24 provides a perspective view of another illustrative valve device of the invention.

DETAILED DESCRIPTION

Figure 4:
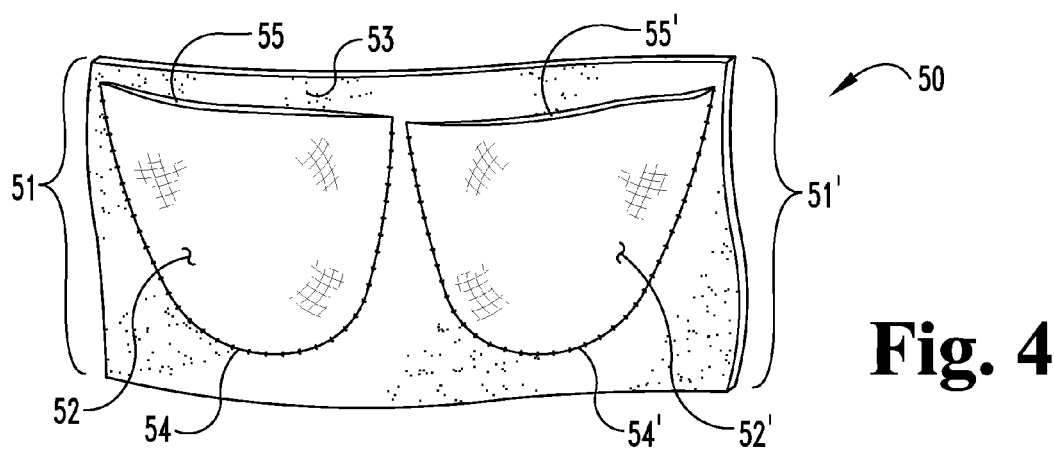
FIG. 4 provides a perspective view of an illustrative valve-forming sheet of the invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, the present invention provides vascular valve devices, as well as systems and methods for the delivery thereof. In preferred embodiments, the invention provides a prosthetic valve device for implantation in a vein to treat venous insufficiency. The device includes one or more leaflets disposed within and attached to a frameless conduit, wherein the conduit is sufficiently constructed to allow for secure attachment to a wall of a vein. The leaflets and the conduit are formed with a flexible material, and in certain embodiments, the flexible material comprises a remodelable material.

With reference now to FIG. 1, shown is a perspective view of an illustrative valve device 30 of the present invention. Device 30 includes a first leaflet 31 and a second leaflet 32 disposed within a stentless or frameless conduit 33. The leaflets 31 and 32 and the conduit 33 are formed with a flexible material. In certain embodiments, the leaflets and/or the conduit comprise a remodelable material and/or a synthetic polymeric material. Although the present embodiment provides a bi-leaflet valve, it will be understood that the invention disclosed herein includes devices having one, two, three, or any practical number of leaflets.

The first leaflet 31 and second leaflet 32 have fixed edges 34 and 35, respectively, which are attached to inner walls of the conduit 33. The first leaflet 31 and second leaflet 32 also have free edges 36 and 37, respectively, that are not attached to inner walls of the conduit 33. The fixed edges 34 and 35 may be attached to the conduit 33 in any suitable manner, including but not limited to suturing, stapling, bonding, laser welding, and the like. In certain embodiments of the invention, the device 30 is configured so that portions of the leaflets' outer edges can protrude through slits or holes in the conduit, and thereby directly contact vessel walls upon implantation of the device within a vascular vessel (see, e.g., FIG. 16). In these embodiments, small intestinal submucosa (SIS) is particularly suitable for forming the leaflets, since SIS induces host tissue proliferation and leads to the remodeling and regeneration of appropriate tissue structures upon in vivo implantation.

In operation, the first leaflet 31 and second leaflet 32 facilitate valve function by selectively allowing blood flow in a first direction, and selectively restricting blood flow in a second direction opposite the first direction. In particular, the leaflets 31 and 32 move outwardly to open the valve 30 when subjected to blood flow in the direction of the arrow, and move inwardly to close the valve 30 when subjected to blood flow in a direction opposite that of the arrow. As illustrated, the device 30 is designed to facilitate net blood flow in the direction of the arrow.

One aspect of the device 30 is that it is not necessary to attach the first leaflet 31 or second leaflet 32 to the vessel wall when implanting the device. Instead, the conduit 33 is attached to the vessel wall, with the leaflets already secured to the conduit. This aspect of the device 30 is particularly advantageous, because it eliminates, or at least reduces, the risk of damaging or improperly orienting the leaflets during the implantation procedure.

To assist in implantation of the device 30, the conduit 33 can incorporate a variety of adaptations for attachment to vessel walls, including but not limited to elements configured to partially or completely penetrate the walls. For example, vessel-wall-penetrating elements, such as barbs or hooks can be incorporated into the conduit 33. As illustrated in FIG. 1, a plurality of barbs 38 are provided on both ends of the conduit 33 to secure the conduit to the vessel wall. Alternatively or in addition, the conduit 33 can be provided with a biocompatible adhesive sufficient to secure the conduit 33 to the vessel wall. A range of biocompatible and potentially also biodegradable adhesives are known and can be used in the present invention for this purpose. Moreover, the conduit 33 can be provided with the adhesive in any suitable manner, including, for example, applying an amount of adhesive on an outer surface of the conduit 33 that will come into contact with the vessel wall. In still further embodiments of the invention, the adhesive can be applied in situ in the vessel to the conduit 33, and/or to corresponding areas of the vessel wall, using a catheter or other suitable delivery device.

The frameless conduit 33 depicted in FIG. 1 is formed with a seamless tube of material. In other embodiments of the invention, the conduit 33 is formed with a generally square or generally rectangular sheet of material rolled into a tube and having a seam (see, e.g., FIG. 9). Regardless of how the conduit 33 is formed, it is understood that the size, shape, and configuration of the conduit (as well as any other component of the device 30) can vary depending on the requirements of a particular implantation procedure, situation, or patient. For example, the device 30 can be configured for implantation within the vascular system of a patient, and in some embodiments, constructed so as to have predetermined dimensions, such that the device is adapted to provide a valve function in a vein or other vessel of a specific diameter. In other embodiments, the dimensions of the device can be selected so as to render the device suitable for providing a valve function in a vein or other vessel having an inner diameter of about 5 mm to about 25 mm, more typically in the range of about 8 mm to about 20 mm.

The remodelable material of the present invention (e.g., the material used to form the conduit 33 of FIG. 1) can be formed with a generally biocompatible and remodelable extracellular matrix material. Suitable ECM material of the present invention can be derived from a variety of natural sources, including pericardial tissues (e.g., pericardial sacs), amniotic sacs, connective tissues, bypass grafts, skin patches, blood vessels, cartilage, dura mater, skin, fascia, umbilical tissues, renal capsule membrane, serosa, peritoneum, basement membrane materials (e.g., liver basement membrane), submucosa and the like. Remodelable materials are derived from a particular animal species, typically mammalian, such as human, bovine, equine, ovine, or porcine. These materials may include a portion of an organ or structural tissue components of an organ. Moreover, suitable remodelable tissues include xenografts (i.e., cross species, such as a non-human donor for a human recipient), allografts (i.e., interspecies with a donor of the same species as the recipient) and autografts (i.e., the donor and the recipient being the same individual). Suitable remodelable tissue is generally soft tissue. In certain embodiments, the remodelable material is fully or partially crosslinked as discussed in detail below.

The submucosal tissue of cattle, sheep, and other warm-blooded vertebrates, especially pigs, provides a particularly preferred material for use in the present invention. A favorable characteristic of remodelable submucosal tissue (e.g., small intestinal submucosa, stomach submucosa, urinary bladder submucosa, or uterine submucosa) is that it has the capacity to induce host tissue proliferation and lead to the remodeling and regeneration of tissue structures upon in vivo implantation.

Submucosal tissue may, for example, be prepared as described in U.S. Pat. Nos. 4,902,508; 5,554,389; and 6,206,931. Again, it should be understood that submucosa can be derived from any suitable organ or other biological structure, including for example, submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. Thereafter, the submucosa can be assembled into tissue segments (e.g., sheets, strands, and other shapes) or stored for later processing.

An artificial implant device of the invention may also be derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

The remodelable ECM material may be manipulated before or after it is assembled into a component of the present invention. For example, the material may be cut, trimmed, sterilized, and/or treated with one or more property modifiers. In certain embodiments, the ECM material is crosslinked before or after any preliminary processing and/or storage. Crosslinking tends to fix ECM material in the shape imposed during the crosslinking process. However, because certain crosslinking agents and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Following any crosslinking, the material can be further processed, which can involve additional chemical and/or mechanical manipulation of the material, as well as processing the material into the desired invention component.

Crosslinking, in addition to providing mechanical stabilization (e.g., by anchoring the collagen fibrils and preventing enzymatic degradation of the tissue), can decrease or eliminate antigens in the tissue. Glutaraldehyde, formaldehyde or a combination thereof is typically used for fixation, but other fixatives can be used, such as epoxides, epoxyamines, diimides and other difunctional/polyfunctional aldehydes. In particular, aldehyde functional groups are highly reactive with amine groups in proteins, such as collagen. Epoxyamines are molecules that generally include both an amine moiety (e.g. a primary, secondary, tertiary, or quaternary amine) and an epoxide moiety. The epoxyamine compound can be a monoepoxyamine compound and/or a polyepoxyamine compound.

In addition to being crosslinked, the material can be treated (e.g., brought into contact, impregnated, coated, etc.) with one or more desirable compositions, such as anticoagulants (e.g., heparin), growth factors, other desirable property modifiers, and the like to modify the tissue properties. Specifically, the tissue can be treated with an anticalcification agent to reduce calcification of the tissue following implantation and/or to encourage tissue remodeling. Generally, any calcification reducing agents would be contacted with the composite matrix following crosslinking, although some calcification reducing agents can be contacted with the tissue prior to crosslinking. Suitable calcification reducing agents include, for example, alcohols, such as ethanol and propylene glycol, detergents (e.g., sodium dodecyl sulfate), toluidine blue, diphosphonates, and multivalent cations, especially $Al^{+3}$, $Mg^{+2}$ or $Fe^{+3}$, or corresponding metals that can oxidize to form the multivalent metal cations.

Additionally, to encourage ingrowth of viable cells, the tissue can be treated to reduce or eliminate toxicity associated with aldehyde crosslinking and/or associated with compounds that stimulate the infiltration of the tissue by desirable cells. Further, the tissue can be crosslinked with dialdehydes or the like to reduce or eliminate any cytotoxicity. Suitable compounds for reduction of aldehyde cytotoxicity include, for example, amines, such as amino acids, ammonia/ammonium, sulfates, such as thiosulfates and bisulfates, surfactants and combinations thereof.

As prepared, the ECM material may optionally retain various bioactive components native to the source tissue. For example, the ECM material may include one or more growth factors, such as basic fibroblast growth factor (FGF-2), transforming growth factor beta (TGF-beta), epidermal growth factor (EGF), and/or platelet derived growth factor (PDGF). Further, the submucosa or other ECM material of the present invention may include other biological materials, such as heparin, heparin sulfate, hyaluronic acid, fibronectin and the like. Thus, generally speaking, the ECM material may include a bioactive component that induces, directly or indirectly, a cellular response, such as a change in cell morphology, proliferation, growth, protein or gene expression, which again, is desirable for promoting tissue ingrowth into one of the components of the present invention.

In addition to, or as an alternative to, the inclusion of such native bioactive components, non-native bioactive components, such as those synthetically produced by recombinant technology or other methods, may be incorporated into the ECM material. The addition of a non-native component, e.g., a growth factor, with a tissue matrix may involve direct attachment, application of a coating, including an adhesive or binder, or chemical binding, involving a binding agent.

The ECM material used in the invention is preferably highly purified, for example as described in U.S. Pat. No. 6,206,931. Thus, the preferred material will exhibit an endotoxin level of less than about 12 endotoxin units (EU) per gram, more preferably less than about 5 EU per gram, and most preferably less than about 1 EU per gram. As additional preferences, the ECM material may have a bioburden of less than about 1 colony forming units (CFU) per gram, and more preferably less than about 0.5 CFU per gram. Fungus levels are desirably low as well, for example less than about 1 CFU per gram, and more preferably less than about 0.5 CFU per gram. Nucleic acid levels are preferably less than about 5 μg/mg, and more preferably less than about 2 μg/mg, while virus levels are preferably less than about 50 plate forming units (PFU) per gram, and more preferably less than about 5 PFU per gram. These and additional properties of submucosa taught in U.S. Pat. No. 6,206,931 may be characteristic of the ECM material used in the present invention.

FIGS. 2 and 3 are illustrative of certain valve device configurations for providing valve function in a tubular body passageway. In particular, FIG. 2 illustrates a top view of the valve device 30 of FIG. 1 implanted or engrafted within a vascular vessel 39, the valve 30 in a generally open condition. The device 30 can be attached to the vessel in any suitable manner, including but not limited to those previously described. As depicted, the first leaflet free edge 36 and the second leaflet free edge 37 are configured to move toward and away from one another to close and open, respectively, the valve orifice 40.

Turning now to FIG. 3, shown is a side view of the implanted valve device 30 of FIG. 1, showing a potential attachment path (in phantom) for the fixed edges 34 and 35 of the leaflets extending in a direction generally both longitudinally and circumferencially around the conduit 33. It will be understood that the leaflets could be attached to the conduit along such a path in any suitable manner, including but not limited to utilizing mechanical elements, bonding, and/or welding.

Referring now to FIG. 4, shown is an illustrative valve-forming member 50, which can be manipulated to form a valve device within the scope of the present invention. In particular, a generally cylindrical valve can be formed by circularizing the member 50 and connecting the member's opposing sides 51,51'. The opposing sides 51, 51' can be joined in any suitable manner, including but not limited to using staples, an adhesive, and the like.

The member 50 includes a pair of leaflets 52, 52' attached to a sheet of material 53, wherein the leaflets and the sheet are both formed with a flexible material. In the current embodiment, portions of the leaflets' edges are sutured to the sheet to provide fixed edges 54,54'. The leaflets' upper edges are unstitched to provide free edges 55,55'. In further embodiments, the fixed edges 54,54' are attached to the sheet using other suitable means, including but not limited to tissue welding, stapling, and the like. As with any leaflet of the present invention, the leaflets 52,52' can have a variety of sizes, shapes, and orientations. Also, it should be appreciated that the leaflets 52,52' can be manipulated before or after the sheet is circularized, and the leaflets can be attached to the sheet 53 before or after the sheet is formed into a tube.

Figure 5:
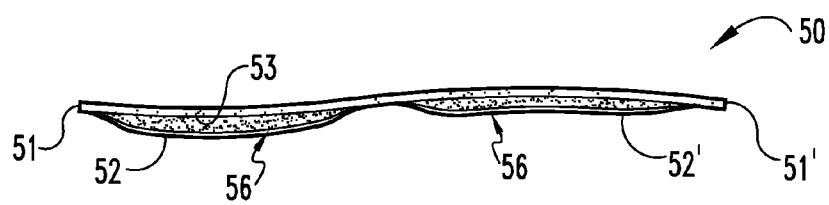
FIG. 5 provides a top view of the valve-forming sheet of FIG. 4.

FIG. 5 is a top view of the valve-forming member 50 of FIG. 4. As illustrated, the leaflets 52, 52' provide slack 56 in the leaflet material when attached to the sheet 53. The extent of the slack 56 typically depends on the size, shape, and/or configuration of the leaflets selected. However, in certain embodiments, the slack 56 can be manipulated before, during, or after the leaflets are attached to the sheet. For example, the leaflets may be chemically or physically altered to change the flow characteristics of the to-be-formed valve. In these embodiments, various slack 56 configurations can be designed through routine experimentation so as to allow for optimal blood flow back to the heart.

Figure 6:
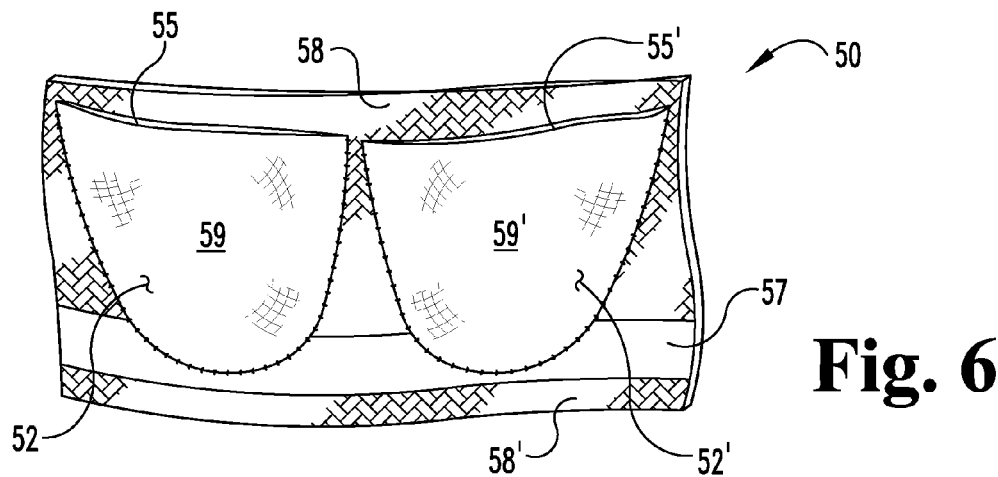
FIG. 6 provides a perspective view of another valve-forming sheet of the invention.

Referring now to FIG. 6, shown is a valve-forming member 50 embodiment, which is similar to the valve-forming member shown in FIG. 4 except that the sheet of material 53 provides a segment of remodelable material 57 flanked by two segments of synthetic polymeric material 58,58'. The synthetic material segments 58,58' eliminate, or at least reduce, the risk of certain portions of the leaflets, especially the leaflets' center regions 59,59' and free edges 55,55', from adhering to inner conduit walls when the valve is implanted in a patient. To the contrary, the remodelable material segment 57 is configured to promote tissue ingrowth into the remodelable material segment 57 from inner walls of a tubular body passage, and thereby facilitate remodeling of the remodelable material leaflets 52,52'. In certain embodiments, portions of the remodelable material segment are removed so that the leaflets can directly contact inner vein walls upon implantation. In still other embodiments, the synthetic material segments and/or the remodelable material segment comprise a mesh material, such as polyglycolic acid (PGA) or the like, to promote tissue ingrowth into the segments. The mesh can be designed to degrade or be resorbed by the body after portions of the leaflets have been incorporated into the vessel wall and at least partially replaced by adjacent native tissue.

Figure 7:
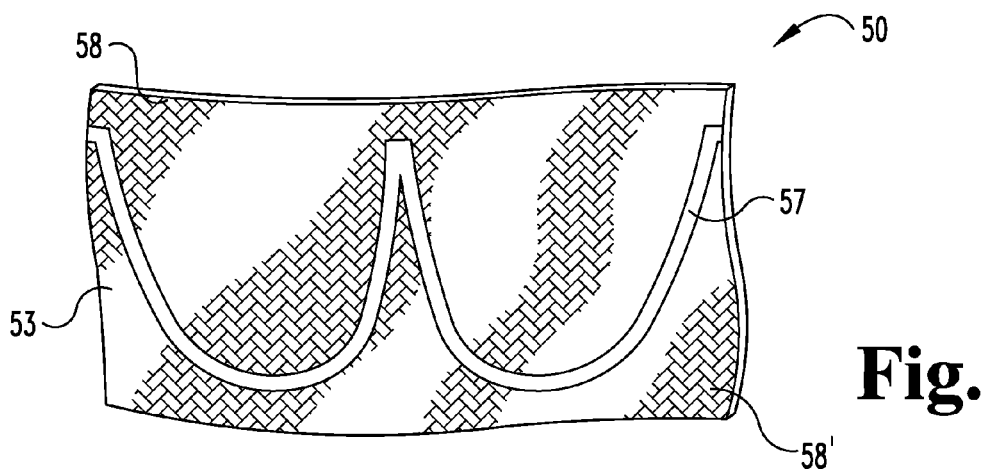
FIG. 7 provides a perspective view of an illustrative conduit-forming sheet of the invention.

In other embodiments of the invention, the sheet of material 53 provides any practical combination of remodelable material segments and/or synthetic material segments, wherein the size, shape, and configuration of any segment of material can vary depending on the requirements of a particular application. For example and referring now to FIG. 7, shown is a valve-forming member 50 embodiment, wherein the sheet 53 provides two synthetic polymer segments 58,58' separating a remodelable material segment 57 having a W-shaped contour. (In this illustration, the leaflets are eliminated for clarity.) The sheet of material of FIG. 7 is similar to the sheet of material of FIG. 6 except that the segment of remodelable material 57 is configured to contact more of the leaflets' material, and consequently facilitate greater tissue ingrowth into the leaflets from inner walls of the tubular body passage.

A variety of synthetic polymeric materials may be utilized in the present invention (e.g., to form the segments 58,58'). The synthetic polymeric material can be either a bioresorbable and/or non-bioresorbable plastic. Bioresorbable, or bioabsorbable polymers that could be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes.

Suitable non-bioresorbable, or biostable polymers that could be used include, but are not limited to, polytetrafluoroethylene (PTFE) (including expanded PTFE) and/or polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate. The material may be in the form of yarns, fibers, and/or resins, monofilament yarns, high tenacity polyester. Further, the present application contemplates other plastic, resin, polymer, woven, and fabric surgical materials, other conventional synthetic surgical materials, such as a shape-memory plastic, and/or combinations of such materials.

Figure 8:
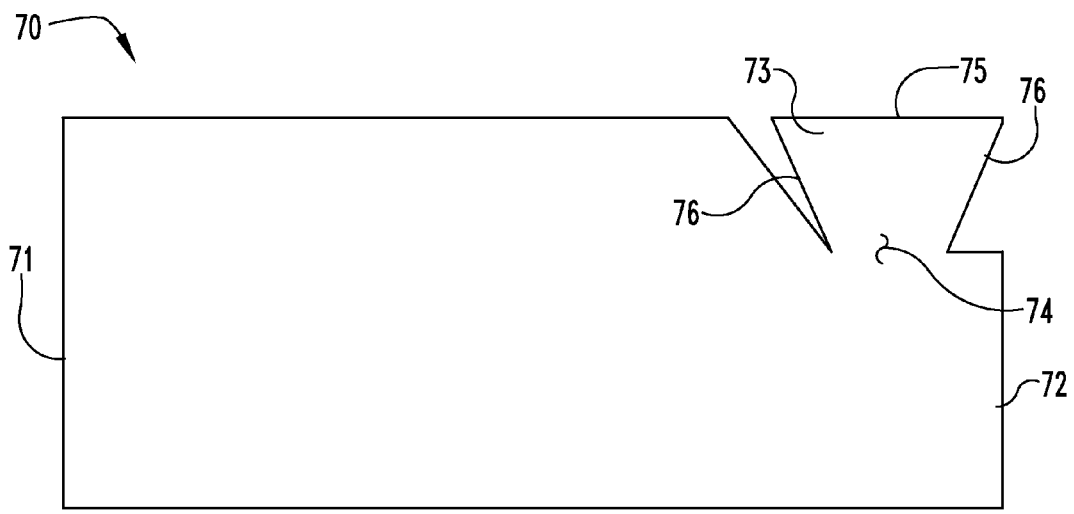
FIG. 8 provides a front view of an illustrative valve-forming sheet of the invention.

Referring now to FIG. 8, shown is an illustrative valve-forming sheet 70 of the present invention. To form a frameless valve within the scope of the present invention, the sheet 70 is circularized, whereupon opposing sides 71 and 72 of the sheet are connected to form a conduit. The sheet 70 is formed with a flexible material. In certain embodiments, the sheet 70 comprises a remodelable material and/or a synthetic polymeric material. As depicted, one corner of the sheet provides a leaflet-forming portion 73 having a base 74 integral with the sheet, a top edge 75, and diverging sides 76. Upon circularization of the sheet, the leaflet-forming portion 73 provides a single leaflet disposed within the frameless conduit.

The leaflet-forming portion 73 can have a variety of shapes, sizes, and/or orientations. For example, in certain embodiments of the invention, the leaflet-forming portion has a top and/or sides that are curvilinear. In other embodiments, the top edge 75 provides material extending beyond the top edge of the sheet 70. In still further embodiments, the leaflet-forming portion 73 can be sufficiently dimensioned so that upon circularization of the sheet 70, the leaflet can extend across the inner passageway of the conduit and co-apt with opposing walls of the conduit to selectively restrict blood flow through the valve (see FIGS. 9 and 10). However, let it be understood that the leaflet-forming portion can also be manipulated (e.g., chemically or physically altered) at any time before or during the circularization of the sheet.

Continuing with FIG. 8, it is further understood that the valve-forming sheet 70 can provide a plurality of leaflet-forming portions 73. For example, a valve-forming sheet having a pair of leaflet-forming portions can be used to form a bi-leaflet valve. In this case, the leaflet-forming portions can be dimensioned so that upon circularization of the sheet, the leaflets can co-apt with each other within the inner passageway of the conduit, e.g., near the middle of the inner passageway. Further, the leaflet-forming portion 73 may be formed in any suitable manner, including but not limited to using a die cutting machine, pair of scissors, or other cutting device.

Figure 9:
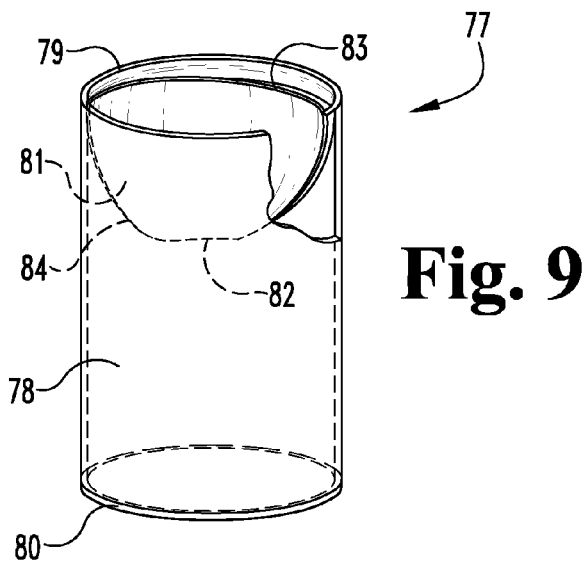
FIG. 9 provides a front, perspective view of a valve device formed with the valve-forming sheet of FIG. 8.
Figure 10:
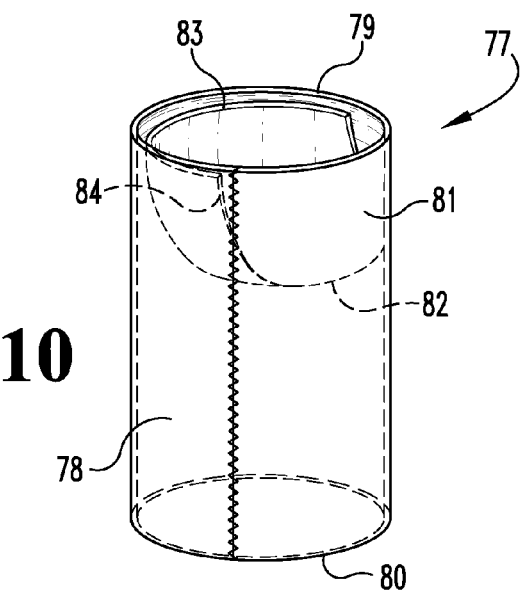
FIG. 10 provides a side, perspective view of the valve device of FIG. 9.

FIGS. 9 and 10 show a front and side view, respectively, of a valve prosthesis 77 formed with the valve-forming sheet 70 of FIG. 8. The prosthesis 77 is formed (at least in part) by circularizing (and connecting opposing sides of) the sheet to form a generally cylindrical conduit 78. The frameless conduit 78 has a first end 79 and a second end 80, with the normal, antegrade flow of blood typically traveling from the second end 80 to the first end 79, the latter being located closest to the heart when the prosthesis is deployed at a venous site within the lower extremities of a patient. In the current embodiment, opposing sides of the sheet are held together with sutures. However, in other embodiments, other suitable means are used to make this connection, including but not limited to applying an adhesive, staples, and the like.

In certain embodiments, the first end 79 and/or the second end 80 have a reinforced lip. A reinforced lip may be made by folding, rolling, or otherwise gathering and securing material proximate the ends of the conduit 78. Alternatively, a different material may be secured to the first end 79 and/or the second end 80 to provide the lip or other reinforcement. Still further, the first and second ends 79 and 80 may be integrally made with a reinforced lip, for example by molding, and/or treating material at the first and second ends 79 and 80 to increase its strength relative to the remainder of conduit 78, for example by adding crosslinking to portions of the ends that are made of collagenous materials.

The prosthesis 77 further includes a leaflet 81 having a base 82 integral with the conduit, a top 83, and sides 84. When the valve 77 is deployed in a tubular body passageway, the leaflet 81 moves back and forth in response to changes in hemodynamic pressure. When blood is stagnant or flowing through the passageway in a normal, forward direction, the leaflet 81 remains mostly open. When blood begins to flow in a direction opposite its normal, forward flow, the leaflet 81 moves toward a closed position (as shown in FIGS. 9 and 10). In a closed configuration, the top 83 and sides 84 of the leaflet 81 contact inner walls of the conduit 78 to form a closure or coaptation. In other embodiments, the leaflet is manipulated after the sheet is circularized. For example, portions of the leaflet's top 83 and sides 84 can be sutured or otherwise attached to portions of the conduit. In still other embodiments, material is added to or removed from the leaflet to change the degree of coaptation with the inner conduit walls.

Figure 11:
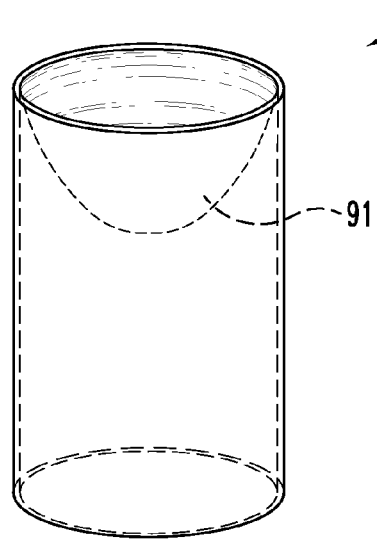
FIG. 11 provides a perspective view of an illustrative valve-forming tube of the invention.
Figure 12:
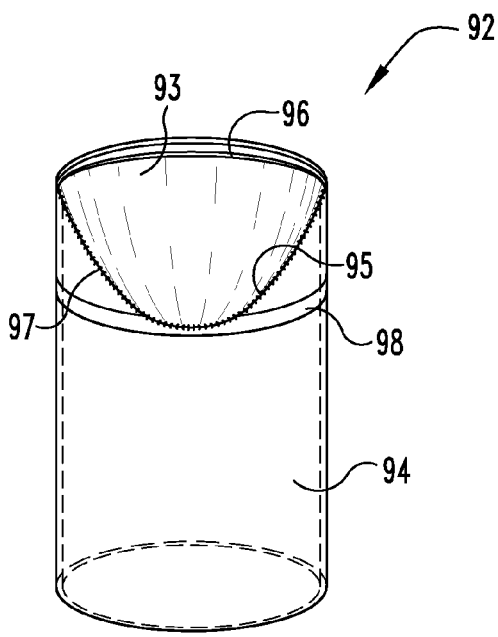
FIG. 12 provides a perspective view of a valve device formed with the valve-forming tube of FIG. 11.

With reference now to FIGS. 11 and 12 together, shown in FIG. 11 is a perspective view of an illustrative valve-forming tube 90 of the present invention. As described herein, the tube 90 can be manipulated to form the frameless valve prosthesis of FIG. 12, although it should be understood that the tube could also be manipulated to form a variety of other frameless valve prostheses within the scope of the present invention. The tube 90 is formed of a remodelable material and provides a leaflet-forming portion 91 at one end. In this illustration, the dotted line generally represents the bottom and side edges of the leaflet-forming portion 91, although in other embodiments, the leaflet-forming portion has a variety of other sizes, shapes, and configurations. For example, the leaflet-forming portion 91 may provide material extending beyond the top of the tube 90. In still other embodiments, a tube 90 embodiment is provided having two or more leaflet-forming portions.

FIG. 12 provides just one valve prosthesis 92 embodiment that can be formed with the valve-forming tube 90 of FIG. 11. The prosthesis includes a leaflet 93 disposed within a frameless conduit 94, the leaflet 93 having a fixed edge 95 integral with the conduit 94 and a free edge 96 non-integral with the conduit 94. In this particular embodiment, portions of the tube 90 proximate the edge of the leaflet-forming portion 91 (dotted line in FIG. 11) are partially bent or creased inward, so that the leaflet-forming portion 91 is disposed within the conduit 94 to form the generally concave leaflet 93. Additionally, sutures 97 are applied along the edge of the leaflet-forming portion 91 to establish the fixed edge 95 of the leaflet 93. The valve 91 also includes a reinforcement element 98 to provide support to portions of the leaflet's fixed edge 95. The reinforcement element 98 may comprise a band or ring of remodelable and/or synthetic material. In still other embodiments, portions of the tube proximate the edge of the leaflet-forming portion are cut or separated to help dispose the leaflet-forming portion within the conduit. In these embodiments, sutures or other suitable attachment means can be used to rejoin the separated portions or otherwise attach the separated portions to the conduit.

Figure 13:
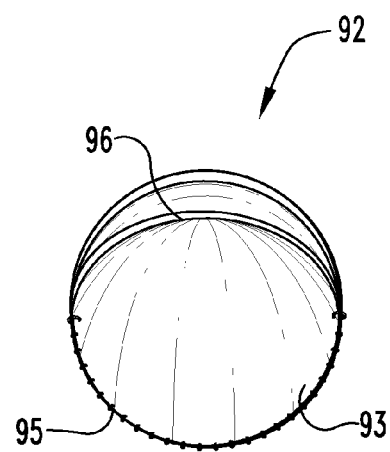
FIG. 13 provides a top view of the valve device of FIG. 12.
Figure 14:
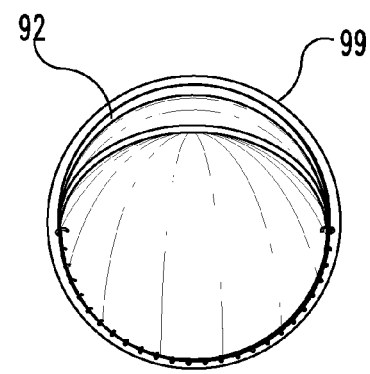
FIG. 14 provides a top view of the valve device of FIG. 12, wherein the conduit is received within a second, outer conduit.

FIG. 13 provides a top view of the valve 92 of FIG. 12, highlighting the fixed edge 95 and free edge 96 of the leaflet 93. When the valve 92 is deployed in a tubular body passageway, the leaflet's free edge 96 moves back and forth in response to changes in hemodynamic pressure. In this illustration, the valve 92 is in a mostly closed condition, a result typically achieved during reverse blood flow. FIG. 14 provides another embodiment of the device 92, which is similar to that shown in FIG. 13 except that the frameless valve prosthesis 92 is received within (and attached to) a reinforcement conduit 99.

Figure 15:
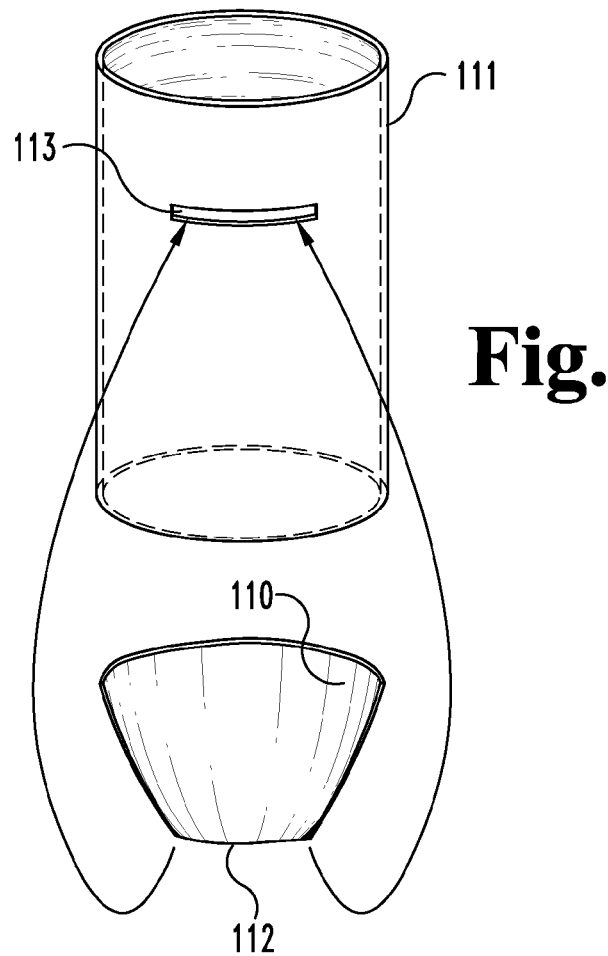
FIG. 15 provides a perspective view of an illustrative leaflet and frameless conduit of the invention, wherein the conduit has a slit in a side wall thereof to receive the leaflet.

Referring now to FIG. 15, shown are perspective views of an illustrative leaflet 110 and an illustrative conduit 111, which can be combined to form a frameless valve prosthesis of the present invention. The leaflet 110 has a base 112, and the conduit 111 has a slit 113 in a side wall thereof, which is configured to receive at least a portion of the leaflet 110 therethrough. Both the leaflet 110 and the conduit 111 can be formed with a remodelable material and/or a synthetic polymeric material, and both can have a variety of shapes, sizes, and configurations. For example, the conduit 111 can be suitably dimensioned for implantation within the vascular system of a patient, and the leaflet 100 suitably dimensioned to provide a valvular function within the conduit 111. In certain embodiments of the invention, the surface area of the leaflet can be slightly smaller or slightly larger than the lateral cross-sectional area of the conduit.

Figure 16:
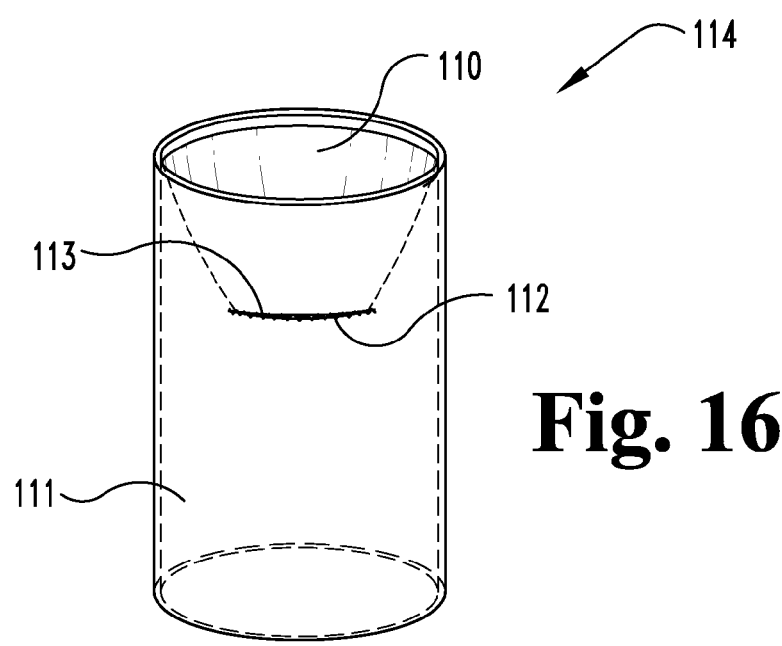
FIG. 16 provides a perspective view of a valve device formed with the leaflet and conduit of FIG. 15.

FIG. 16 shows a perspective view of an illustrative valve prosthesis 114 of the present invention. The prosthesis 114 includes a leaflet 110 disposed within a frameless conduit 111, wherein the leaflet base 112 is received through the slit 113 in the side wall of the conduit 111, and the slit 113 is sewn shut with sutures, the sutures also connecting the leaflet 110 to the conduit 111.

Figure 17:
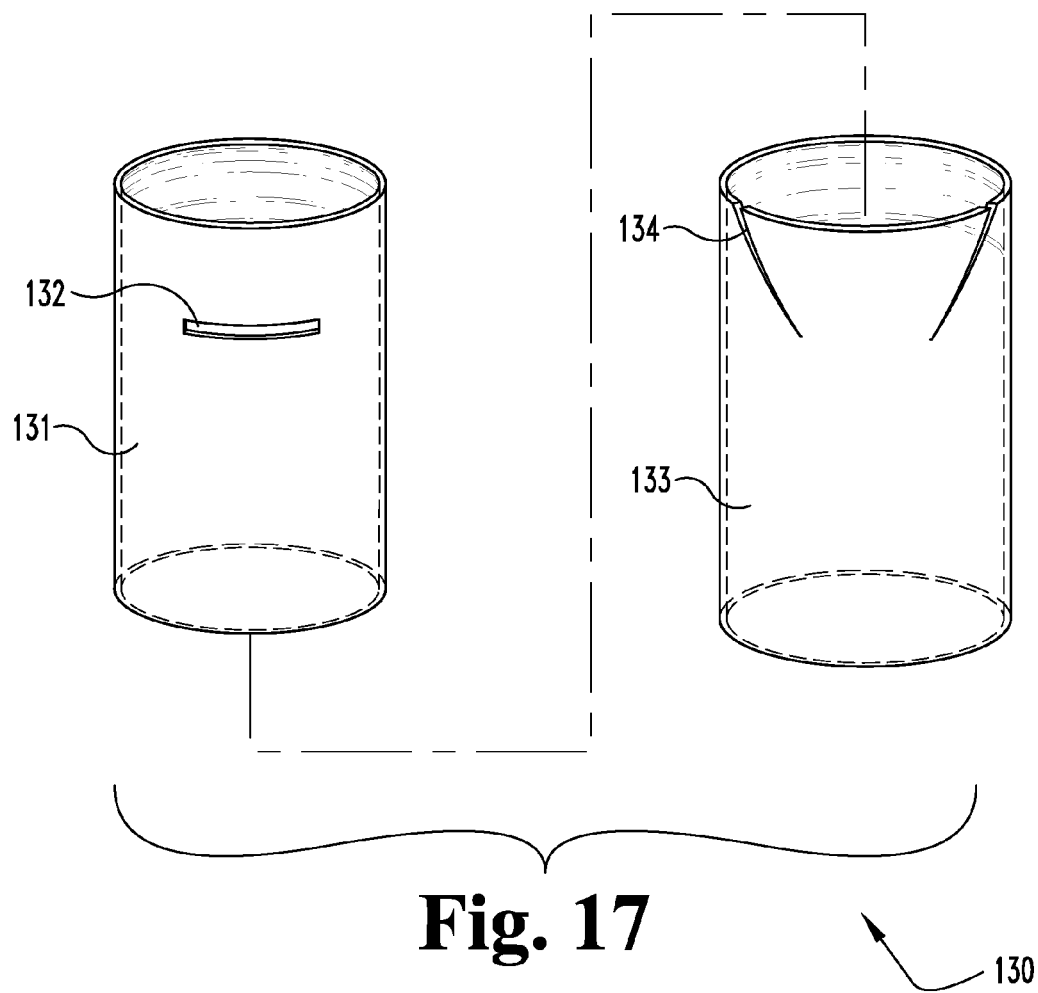
FIG. 17 provides a perspective view of an inner conduit receivable within an outer conduit, whereby the inner conduit has a slit in a side wall thereof to receive an outer conduit leaflet.
Figure 18:
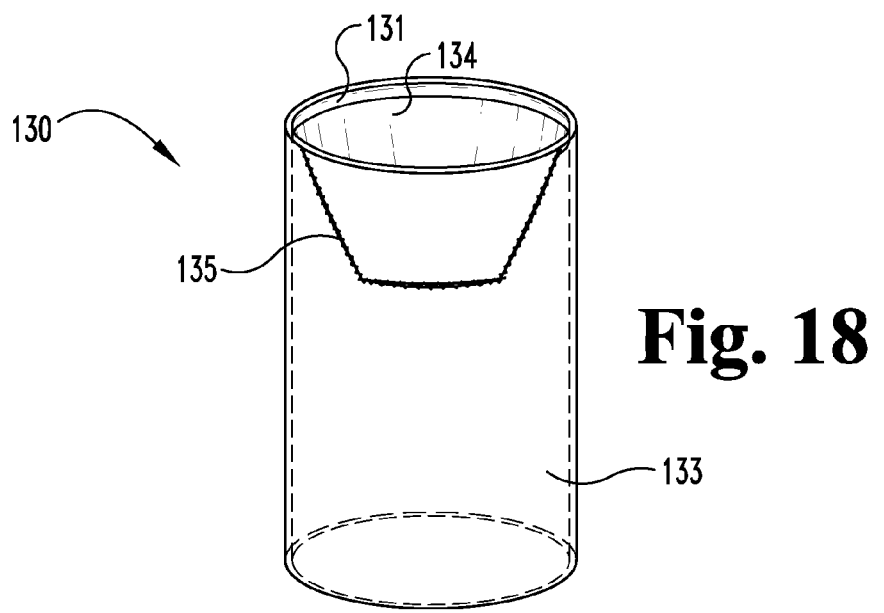
FIG. 18 provides a perspective view of an illustrative valve device formed by receiving the inner conduit of FIG. 17 within the outer conduit of FIG. 17.

With reference now to FIGS. 17 and 18 together, shown in FIG. 17 is an exploded perspective view of an illustrative vascular valve device 130 of the present invention. Device 130 includes an inner conduit 131, which has a slit 132 in a side wall thereof, and an outer conduit 133, which includes a leaflet 134 having a base integral with the outer conduit. The device 130 is formed in part by receiving the inner conduit 131 concentrically within the outer conduit 133, so that the leaflet 134 passes through the slit 132 in the inner conduit, thereby disposing the leaflet 134 within the inner conduit 131. In certain embodiments of the invention, the inner conduit 131 and outer conduit 133 may or may not be attached to each other. For example and as shown in FIG. 18, a plurality of sutures 135 can be applied to the base and sides of the leaflet 134 to attach the leaflet to portions of the inner conduit 131.

Figure 19:
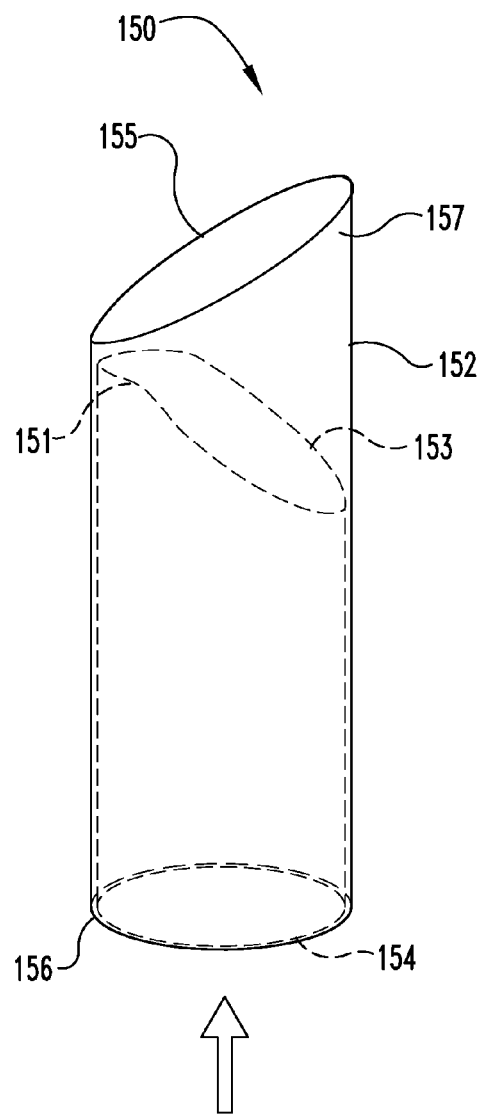
FIG. 19 provides a perspective view of another illustrative valve device of the invention.

Referring now to FIG. 19, shown is a prosthetic valve device 150 embodiment of the present invention. The device 150 includes a semi-rigid, inner conduit 151 received within (and attached to) a flexible, outer conduit 152. The conduits can be attached in any suitable manner, including but not limited to suturing, applying an adhesive, and the like. The inner conduit 151 has a first end 153 and a second end 154, while the outer conduit 152 has a first end 155 and second end 156. The outer conduit first end 155 provides material extending beyond the inner conduit first end 153 to form a leaflet 157. As generally shown in FIG. 19, the inner conduit first end 153 and outer conduit first end 155 are circumferentially tapered but at different angles. The leaflet 157 is configured to facilitate valve function by selectively allowing blood flow in a first direction, and selectively restricting blood flow in a second direction opposite the first direction. Device 150 in particular is designed to facilitate net blood flow in the direction of the arrow. When blood flows opposite the arrow, the leaflet 157 partially collapses as shown in FIG. 20.

Continuing with FIG. 19, both conduits can be formed with a remodelable material and/or a synthetic polymer. For example, in some embodiments of the invention, both conduits are formed with a remodelable material, and the inner conduit 151 is made more rigid than the outer conduit 152 by some form of manipulation, including but not limited to vacuum pressing, cross-linking, freeze drying, and the like. Alternatively, the inner conduit 151 can be formed with a multi-layered tube to increase its rigidity. Nonetheless, it will be understood that in this embodiment, the semi-rigid inner conduit does not constitute a stent, frame, or other valve body support structure, as it does not serve to itself exert radial force upon the vessel walls to retain the position of the device, as would a stent. To the contrary, the inner conduit is flexible enough to take on the configuration to which it is forced, while not having sufficient resiliency or integrity to maintain significant radial force against a vessel wall.

Support structures, e.g., frames, commonly exert significant radial force upon vessel walls, and in certain situations may migrate deleteriously into the walls and/or undesirably reduce the compliancy of the vessel in which they are implanted. As well, such stent or frame structures can present increased risks for thrombosis or embolism.

Figure 20:
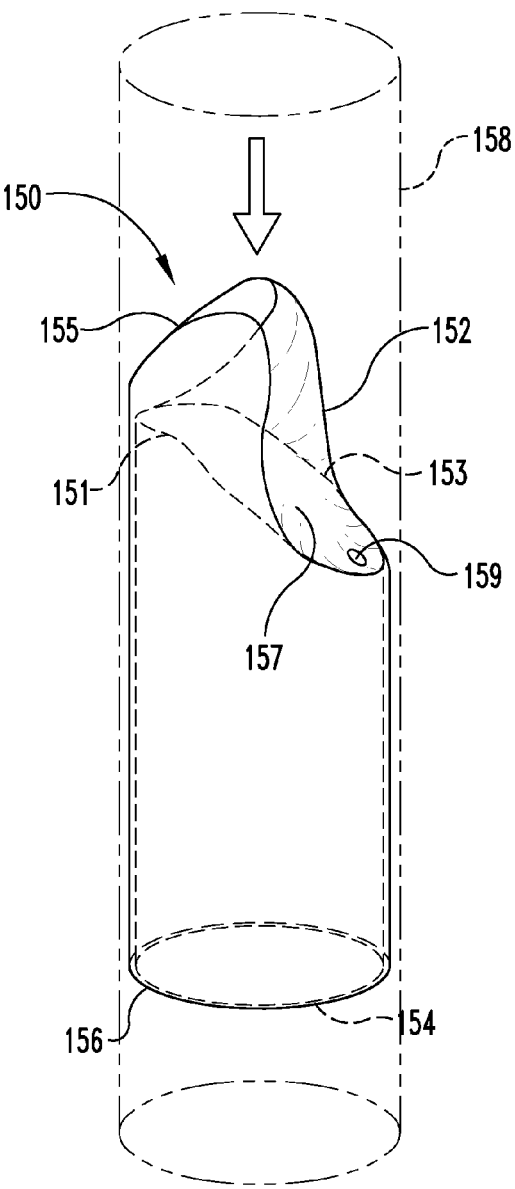
FIG. 20 provides a perspective view of one configuration of the valve device of FIG. 19.

FIG. 20 shows an illustrative valve device 150 implanted within a vascular vessel 158 (e.g. a vein), wherein the device 150 is seated in the vein 158 by attaching portions of the outer conduit 152 to the vein's inner walls. The outer conduit 152 can be attached to the vein 158 using an adhesive or any other means described herein. In certain embodiments of the invention, portions of the leaflet 157 are attached to inner vein walls. However, in other embodiments, no part of the leaflet 157 is attached to the vein. In either case, the portion of the leaflet 157 not attached to the vein is free to move back and forth between a closed position and an open position. The movement or function of the leaflet 157 can be affected by the degree of flexibility of the leaflet material, and therefore, the present invention contemplates leaflet material having various flexibilities.

Continuing with FIG. 20, the leaflet 157 can include a controlled reflux hole 159. The hole 159 is configured to allow an amount of blood to pass through the leaflet 157 when the leaflet is in a generally closed position. The size of the 159 hole, and its location and orientation on the leaflet 157 can vary depending on the amount of controlled reflux desired for a particular valve device.

Figures 21, 22:
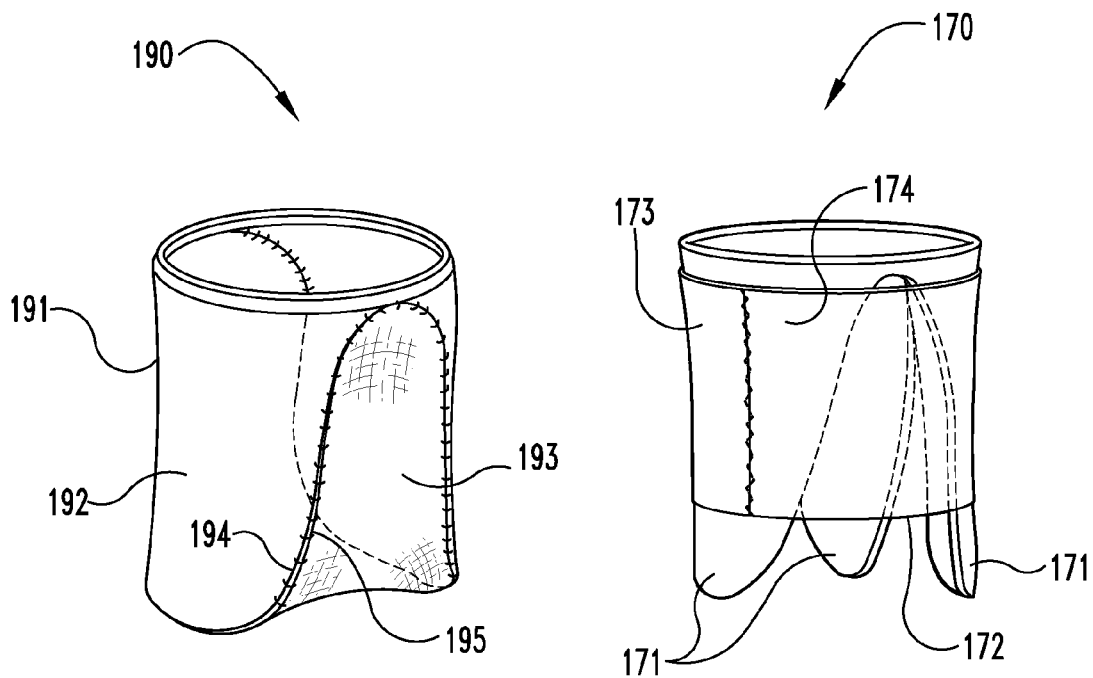
FIG. 21 provides a perspective view of a valve device of the invention.
FIG. 22 provides a perspective view of another valve device of the invention.

Whether formed with a seamless tube of material or a sheet of material rolled into a tube and having a seam, a conduit of the present invention can have a variety of shapes, sizes, and configurations. For example, the conduit 33 depicted in FIG. 1 provides material extending beyond the leaflets in both longitudinal directions. In this configuration, the first leaflet 31 and second leaflet 32 are completely disposed within the conduit. In certain other embodiments of the invention, however, one or more conduits provide material extending beyond the leaflets in neither longitudinal direction or in only one longitudinal direction. For example and referring now to FIG. 21, shown is an illustrative implantable valve device 170 of the present invention, which includes three leaflets 171 disposed within (and attached to) a frameless conduit 172, wherein the size and configuration of the conduit 172 is such that portions of all three leaflets 171 extend beyond the top and bottom, annular edges of the conduit 172. This valve configuration is advantageous, because in addition to providing one or more of the favorable characteristics herein disclosed for the conduits of the present invention, this configuration allows certain portions of the leaflets 171 to contact inner walls of a vein upon implantation, and thereby promotes tissue ingrowth into the leaflets from the inner walls of the vein.

Continuing with FIG. 21, the generally cylindrical conduit 172 comprises a first segment of material 173 sutured to a second segment of material 174. Nonetheless, it is understood that the conduit 172 could be formed with any practical number of segments of material, and that any segment could have a variety of shapes, sizes, and configurations. In certain embodiments, one or both ends of the conduit 172 have substantially the same contour as portions of the leaflets 171. Further, in addition to suturing, the segments could be attached by any other suitable means disclosed herein.

FIG. 22 provides a frameless vascular valve 190 having a conduit 191, wherein the conduit 191 comprises a pair of leaflets 192 and a pair of spanning segments 193. The leaflets, which have opposing sides 194, are configured to selectively restrict blood flow through the valve 190. The spanning segments 193, which have opposing sides 195, are attached to the leaflets 192 in such a way as to form the conduit 191. In particular, each spanning segment 193 spans the distance between adjacent opposing sides 194 of the two leaflets 192. Nonetheless, it is understood that the present invention provides a valve 190 having any practical number of leaflets and/or any practical number of spanning segments. For example, a valve 190 could have three leaflets and three spanning segments. Further, the leaflets 192 and/or the spanning segments 193 can be made of a remodelable material and/or a synthetic polymeric material. In a preferred embodiment, the spanning segments are made sufficiently stiff to hold the shape of the leaflets. In certain embodiments, the spanning segments are made with one or more layers of SIS.

With reference now to FIGS. 23 and 24 together, shown in FIG. 23 is a perspective view of at least one step in a method of manufacturing a prosthetic valve of the present invention. In this method embodiment, a tube of material 210 having a reinforcement band 211 is placed concentrically around an inner mold 212, wherein the inner mold 212 provides a valve-shaping element 213. The tube 210 is positioned on the inner mold 212, so that the reinforcement band 211 is positioned proximate the base of the valve-shaping element 213. Additionally, the tube 210 is received concentrically within an outer mold 214, wherein the outer mold 214 provides its own valve-shaping element 215, which is somewhat larger than the inner mold valve-shaping element 213.

Continuing with FIG. 23, with the tube 210 in a desired position (i.e., between the outside of the inner mold 212 and inside of the outer mold 214), all three devices are subjected to a freeze drying process, whereby a valve prosthesis is formed. Thereafter, the valve prosthesis 216 (see FIG. 24) is removed from the outer mold 214 and inner mold 212. As shown in FIG. 24, the prosthesis 216 includes a bi-leaflet valve element 217 at one end of a frameless conduit 218. The valve element 217 has a reinforced base 219, and is configured to selectively restrict blood flow through the prosthesis 216. In certain embodiments, the prosthesis 216 is further manipulated after being removed from the molds. For example, portions of the prosthesis may be chemically or physically altered (e.g., cut or trimmed) to change the flow characteristics of the prosthesis 216.

Figure 25:
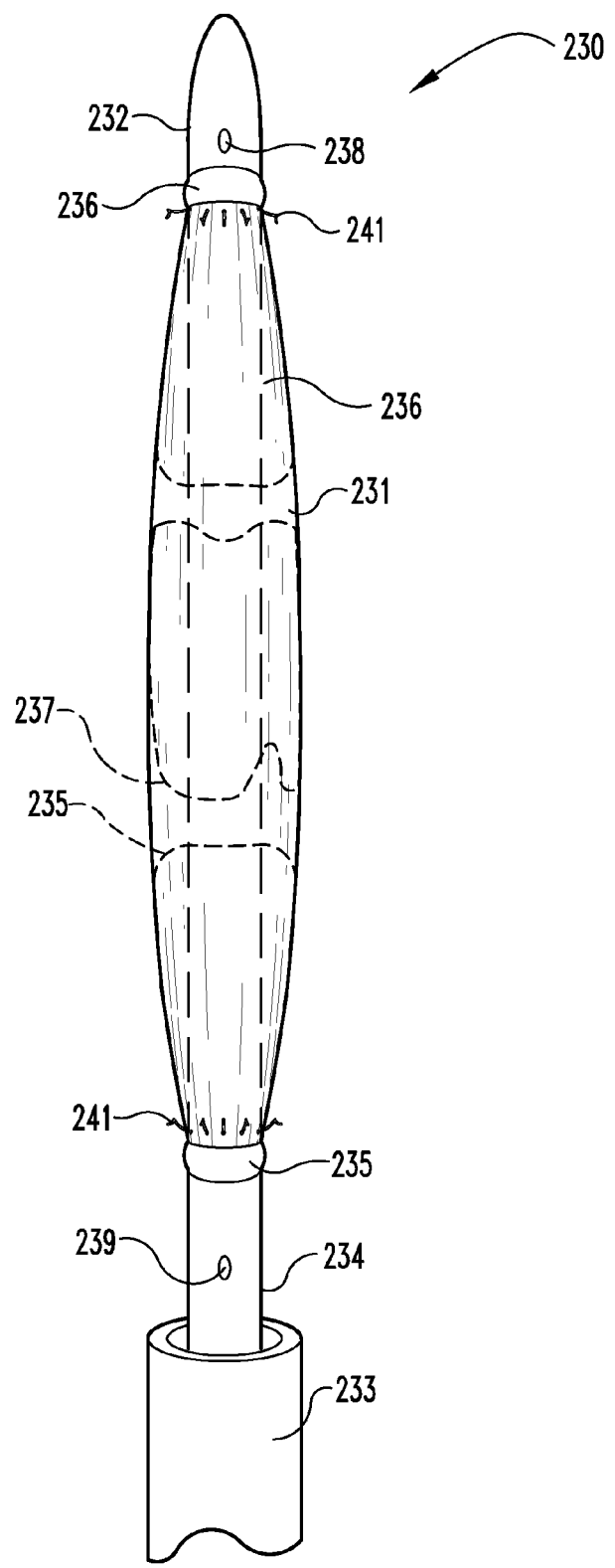
FIG. 25 provides a perspective view of an illustrative medical device of the invention.

With reference now to FIG. 25, shown is a vascular valve deployment system 230 of the present invention. The deployment system includes a valve 231 similar to the valve of FIG. 1 and a delivery device 232, wherein the delivery device includes an outer sheath 233 and a delivery catheter 234 receivable therein. The delivery catheter 234 includes a proximal occlusion element 235 and distal occlusion element 236. In the current embodiment, the valve 231 is received over the catheter 234, such that the proximal and distal occlusion elements 235 and 236 are located (within the valve's conduit) proximally and distally, respectively, of the leaflets 237. In FIG. 25, the sheath is partially withdrawn to more clearly show the valve, catheter, and occlusion elements. The occlusion elements can be provided, for example, by occlusion balloons made of latex, silicone, or any other suitable material. The catheter 234 also includes one or a plurality of distal perfusion opening(s) 238 occurring distally of the distal occlusion element, and one or a plurality of proximal perfusion opening(s) 239 occurring proximally of the proximal occlusion element.

Figure 26:
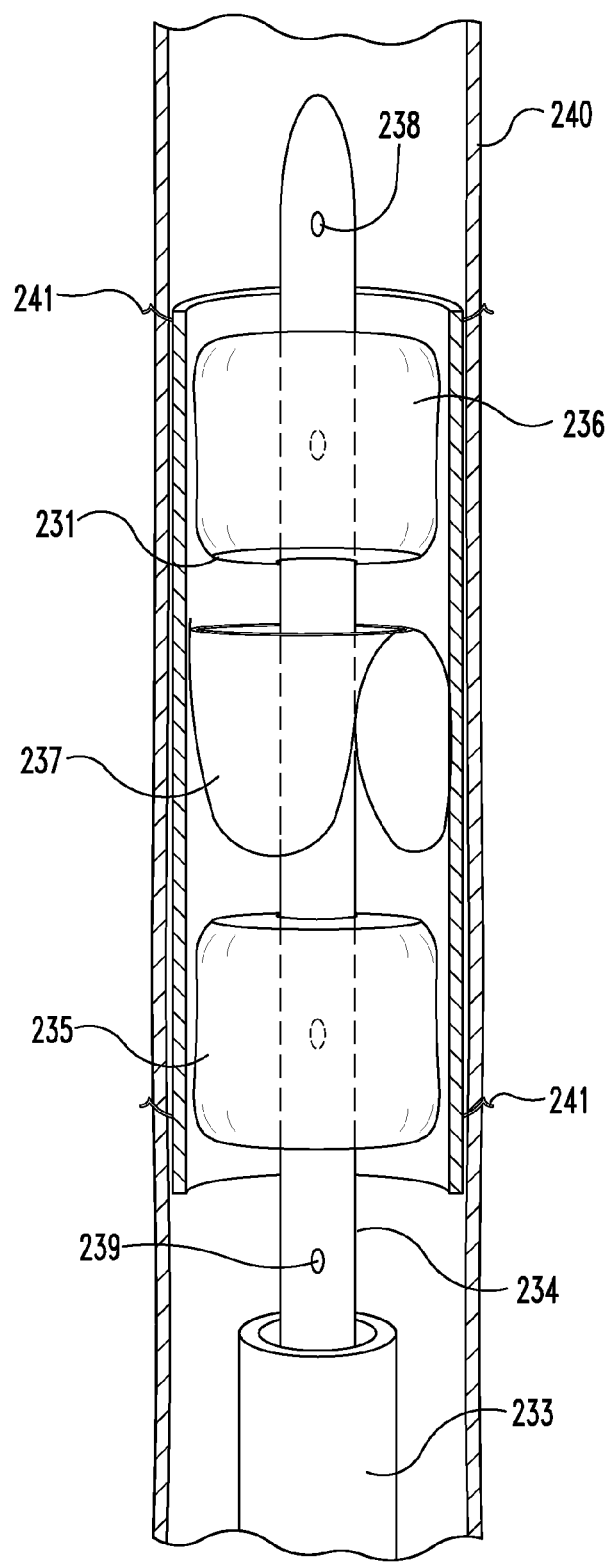
FIG. 26 provides a perspective view of a use of the medical device of FIG. 25.

In use, the system 230 can be introduced into a vascular vessel 240, such as a vein. With the system in a desired position, the sheath 233 can be withdrawn to expose the outer surface of the conduit to the vein's inner walls. Thereafter, the occlusion elements 235 and 236 can be expanded to selectively force portions of the conduit against the inner walls (see FIG. 26). This force may facilitate effective attachment of the valve to the walls using the mechanical or structural wall penetrating elements, and/or adhesives, and/or other techniques described herein. In the current embodiment, the ends of the conduit include barbs 241, such that the barbs at least partially penetrate the vein walls when the proximal and distal occlusion elements 235 and 236 are expanded within the conduit. In this configuration, the occlusion elements are positioned such that they do not exert force on the leaflets 237 when inflated.

After attachment of the valve to the vessel walls, the occlusion elements can be contracted (e.g. deflated in the case of balloons), and the catheter withdrawn back into the sheath, and the sheath/catheter system withdrawn from the patient leaving in place the deployed valve. In addition, it should be noted that during the time in which a segment of the vessel is occluded, the perfusion opening(s) and their associated catheter lumen can allow for perfusion of blood through the occluded segment.

The present invention further provides methods for surgically attaching any of the frameless valve prostheses described herein to a wall of a vein or other vascular vessel. Such a surgical procedure typically comprises suturing or otherwise physically connecting portions of the conduit to the luminal surface of a vein or other vascular vessel. Other potential surgical attachment procedures include, for example, stapling, bonding or otherwise adhering portions of the conduit to the luminal surface of a vein or other vascular vessel. Further, let it be understood that a prosthesis of the present invention can be implanted above, below, or at the location of a native venous valve in the patient. Moreover, a plurality of the prosthetic devices can be implanted in a given vein, to treat venous insufficiency or other similar disorders.

Devices and systems of the invention are desirably adapted for deployment within the vascular system, and in particularly preferred embodiments, devices and systems of the invention are adapted for deployment within the venous system. Accordingly, preferred devices such as device 30 and the others illustrated are adapted as venous valves, for example for percutaneous implantation within veins of the legs or feet, to treat venous insufficiency. In this regard, the frameless nature of valves of the present invention is expected to provide advantages in venous valve function, for example in situations wherein valve function and blood flow is facilitated by adjacent muscle pumps, e.g. in the legs or feet. In these cases, the absence of any frame or support structure exerting substantial radial force upon the venous vessel will allow the vessel to collapse as in native function. As well, such frames or structures can in certain situations undesirably migrate into vessel walls, and/or cause or facilitate thrombus or embolism. The absence of such frames or structures will therefore eliminate these associated factors.

In another embodiment of the invention, a vascular valve kit includes a sealable package and at least one of the vascular valves and/or deployment devices of the present invention. The valve can be placed inside the package, which is unsealed. In other embodiments, the kit is sterilized prior to sealing the package. Sterilization can be achieved via irradiation, ethylene oxide gas, or another suitable sterilization technique. Also, the valve can be in any suitable state (e.g., hydrated, dehydrated, or partially dehydrated). The valve can be dehydrated or partially dehydrated by any means known in the art (e.g., lyophilization or air dried). If a valve of the present application is stored in a dehydrated state, it is preferred that it retains all of its biological and mechanical properties (e.g., shape, density, flexibility, etc.) upon rehydration. The materials and other properties of the packaging will be selected accordingly. For example, in another embodiment, the package is marked to communicate the contents of the package to a person, machine, computer, or electronic device. Such markings may include the size or dimensions of the valve, the type of materials used to form the valve, and the valve's physical state.

In yet another embodiment, the invention provides a vascular valve that includes one or more leaflets disposed within a frameless conduit, wherein the inner conduit surface and/or outer leaflet surface is coated with a hydrophilic or slippery material, such as but not limited to parylene, parafin, and the like, to help prevent the top and inner regions of the leaflets from adhering to the conduit after implantation.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A valve prosthesis suitable for implantation, comprising:
a frameless conduit adapted to attach to a vein wall; and
at least one leaflet disposed within the conduit to selectively restrict blood flow through the conduit, the at least one leaflet configured to capture blood in a pocket formed by the at least one leaflet,
wherein the conduit has an upper conduit portion in which said at least one leaflet is disposed, the upper conduit portion defining an inlet opening for blood inflow and being defined by upper conduit wall portions, and a lower conduit portion occurring below a base of the at least one leaflet, the base of the at least one leaflet defining a lowermost point of the pocket formed by the at least one leaflet, the lower conduit portion defining an outlet opening for blood outflow and being defined by lower conduit wall portions extending below the base of the at least one leaflet;
wherein the pocket formed by the at least one leaflet is configured with an upper opening facing in the direction of the inlet opening and is configured to capture blood flowing from the upper conduit portion to the lower conduit portion to selectively restrict blood flow through the conduit; and
wherein a single sheet of flexible material forms the base of the at least one leaflet and at least a part of the lower conduit wall portions.

2. The valve prosthesis of claim 1, wherein said flexible material comprises a remodelable material.

3. The valve prosthesis of claim 2, wherein said remodelable material comprises an extracellular matrix material.

4. The valve prosthesis of claim 3, wherein said extracellular matrix material comprises serosa, pericardium, submucosa, dura mater, peritoneum, or dermal collagen.

5. The valve prosthesis of claim 1, wherein said flexible material comprises a synthetic polymeric material.

6. The valve prosthesis of claim 1, further comprising at least one anchoring element effective to secure said conduit to the vein wall.

7. The valve prosthesis of claim 1, wherein said conduit comprises a remodelable material.

8. The valve prosthesis of claim 7, wherein said leaflet comprises a synthetic polymeric material.

9. The valve prosthesis of claim 1, wherein said leaflet has an edge for contacting a wall of said conduit.

10. The valve prosthesis of claim 9, wherein said edge is configured to extend longitudinally along and at least partially circumferentially around the conduit wall.

11. The valve prosthesis of claim 9, wherein said edge is attached to said conduit.

12. The valve prosthesis of claim 1, wherein said leaflet has sides attached to said conduit.

13. The valve prosthesis of claim 1, wherein said leaflet provides material extending beyond a top end of said conduit.

14. The valve prosthesis of claim 1, wherein:
said conduit has conduit walls formed with a sheet of material formed into a tube; and
said leaflet is formed by cutting material contiguous with said walls.

15. The valve prosthesis of claim 1, wherein:
said conduit has conduit walls formed with a tube of material; and
said leaflet is formed by cutting material contiguous with said walls.

16. The valve prosthesis of claim 1, wherein:
said conduit includes an inner conduit member and an outer conduit member,
wherein said inner conduit member is received concentrically within said outer conduit member.

17. The valve prosthesis of claim 16, wherein:
said inner conduit member has a slit in a side wall thereof; and
said outer conduit member has said at least one leaflet integrally formed therewith, said at least one leaflet received through said slit to dispose at least a portion of said at least one leaflet within the inner conduit member.

18. The valve prosthesis of claim 17, wherein said inner conduit member is more rigid than said outer conduit member.

19. The valve prosthesis of claim 1, wherein:
said conduit has a slit in a side wall thereof; and
said at least one leaflet has said base received within said slit.

20. The valve prosthesis of claim 19, wherein a portion of said base is configured to contact a wall of a vascular vessel through said slit.

21. The valve prosthesis of claim 1, further comprising:
a first end terminating the upper conduit wall portions; and
a second end terminating the lower conduit wall portions, wherein at least one of the first end or second end includes a reinforced lip.

22. The valve prosthesis of claim 21, wherein the reinforced lip comprises a second material added to the conduit.

23. A method for attaching a frameless valve prosthesis to a vein, comprising:
providing the valve prosthesis of claim 1; and
attaching the frameless valve prosthesis to a wall of a vein.

24. A method of modifying blood flow in a vascular vessel, the method comprising:
percutaneously delivering the valve prosthesis of claim 1 to a site within a vascular vessel; and
percutaneously attaching at least a portion of said valve prosthesis to walls of said vascular vessel, whereby said valve prosthesis selectively permits blood flow in a first direction and selectively restricts blood flow in a second direction.

* * * * *